US011723860B2

(12) United States Patent
Myntti

(10) Patent No.: US 11,723,860 B2
(45) Date of Patent: Aug. 15, 2023

(54) COMPOSITIONS AND METHODS FOR TREATING INTERVERTEBRAL DISCS

(71) Applicant: Next Science IP Holdings Pty Ltd, Chatswood (AU)

(72) Inventor: Matthew F. Myntti, Ponte Vedra Beach, FL (US)

(73) Assignee: Next Science IP Holdings Pty Ltd, Chatswood (AU)

( * ) Notice: Subject to any disclaimer, the term of this patent is extended or adjusted under 35 U.S.C. 154(b) by 0 days.

(21) Appl. No.: 16/765,421

(22) PCT Filed: Nov. 16, 2018

(86) PCT No.: PCT/US2018/061665
§ 371 (c)(1),
(2) Date: May 19, 2020

(87) PCT Pub. No.: WO2019/099932
PCT Pub. Date: May 23, 2019

(65) Prior Publication Data
US 2020/0315956 A1 Oct. 8, 2020

Related U.S. Application Data

(60) Provisional application No. 62/748,431, filed on Oct. 20, 2018, provisional application No. 62/588,401, filed on Nov. 19, 2017.

(51) Int. Cl.
*A61K 9/00* (2006.01)
*A61K 31/194* (2006.01)
*A61P 31/04* (2006.01)

(52) U.S. Cl.
CPC .......... *A61K 9/0024* (2013.01); *A61K 31/194* (2013.01); *A61P 31/04* (2018.01)

(58) Field of Classification Search
None
See application file for complete search history.

(56) References Cited

U.S. PATENT DOCUMENTS

| | | |
|---|---|---|
| 5,661,170 A | 8/1997 | Chodosh |
| 7,959,943 B2 | 6/2011 | Hissong et al. |
| 7,976,873 B2 | 7/2011 | Myntti et al. |
| 7,976,875 B2 | 7/2011 | Myntti |
| 7,993,675 B2 | 8/2011 | Oliver et al. |
| 8,389,022 B2 | 3/2013 | Bignozzi et al. |
| 8,784,790 B2 | 7/2014 | Myntti et al. |
| 8,940,792 B2 | 1/2015 | Myntti |
| 9,314,017 B2 | 4/2016 | Myntti |
| 9,427,417 B2 | 8/2016 | Myntti |
| 10,021,876 B2 | 7/2018 | Myntti |
| 10,166,208 B2 | 1/2019 | Myntti |
| 10,477,860 B2 | 11/2019 | Myntti |
| 10,780,037 B2 | 9/2020 | Myntti |
| 11,090,369 B2 | 8/2021 | Myntti |
| 2013/0244972 A1* | 9/2013 | Ben-Shalom ............ A61K 9/06 514/55 |
| 2016/0073628 A1* | 3/2016 | Myntti ................... A01N 37/02 514/163 |
| 2017/0042848 A1* | 2/2017 | Ala'Aldeen .......... A23L 33/127 |
| 2017/0340590 A1 | 11/2017 | Myntti |
| 2018/0369176 A1 | 12/2018 | Myntti |
| 2019/0262433 A1 | 8/2019 | Myntti |
| 2020/0085037 A1 | 3/2020 | Myntti |
| 2020/0085038 A1 | 3/2020 | Myntti |
| 2021/0037815 A1 | 2/2021 | Myntti |

OTHER PUBLICATIONS

Bustle, "How Swimming In The Ocean Can Mess With Your Skin", https://www.bustle.com/articles/166526-will-ocean-water-heal-a-pimple-the-truth-behind-this-alleged-treatment, accessed Dec. 3, 2021 (Year: 2016).*
BioNumbers, "Osmolarity of sea water", https://bionumbers.hms.harvard.edu/bionumber.aspx?&id=100802&ver=5, accessed Dec. 3, 2021 (Year: 2021).*
McLaughlin et al., "*Propionibacterium acnes* and Acne Vulgaris: New Insights from the Integration of Population Genetic, Multi-Omic, Biochemical and Host-Microbe Studies", Microorganisms, 2019, 7, pp. 128. (Year: 2019).*
Omni Calculator, "Water Viscosity Calculator", https://www.omnicalculator.com/physics/water-viscosity# what-is-the-viscosity-of-water, accessed Dec. 3, 2021 (Year: 2021).*
Flottweg, "Dynamic viscosity", https://www.flottweg.com/wiki/separation-technology/dynamic-viscosity/, accessed Dec. 3, 2021 (Year: 2021).*
Ulivieri et al., "Prevention of post-operative infections in spine surgery by wound irrigation with a solution of povidone-iodine and hydrogen peroxide", Arch Orthop Trauma Surg, (2011), 131, pp. 1203-1206. (Year: 2011).*
Extended search report in EP 188791170.1, dated Nov. 23, 2020.
Bo Li, MD et al, "Association Between Lumbar Disc Degeneration and *Propionibacterium acnes* Infection", SPINE, vol. 41, No. 13, 2016, pp. E764-E769.

(Continued)

*Primary Examiner* — Dominic Lazaro
(74) *Attorney, Agent, or Firm* — Element IP, PLC; David G. Burleson

(57) ABSTRACT

A biocompatible antimicrobial composition effective against microbial biofilms, including in vivo biofilms containing gram-positive bacteria, can be delivered to and used near the spinal column of vertebrates. Once introduced to an area colonized with a bacterial biofilm, particularly an intervertebral disc, the antimicrobial composition weakens the EPS/ECPS macromolecules of the biofilm, which makes the entire biofilm structure susceptible to being dislodged from the affected area or biosorbed. Additionally or alternatively, certain of the subcomponents of the solute component, as well as perhaps the organic liquid(s) of the solvent component, might lyse microbes, particularly gram-positive bacteria, previously protected by the EPS/ECPS macromolecules. Swelling of and around previously impacted intervertebral discs can be reduced or eliminated, often resulting in appreciable reductions in patient pain levels.

12 Claims, No Drawings

(56) References Cited

OTHER PUBLICATIONS

Manu N. Capoor et al, "Prevalence of *Propionibacterium acnes* in Intervertebral Discs of Patients Undergoing Lumbar Microdiscectomy: A Prospective Cross-Sectional Study", PLOS One, Aug. 18, 2016, 8 pages.

Manu N. Capoor et al, "*Priopionibacterium acnes* biofilm is present in intervertebral discs of patients undergoing microdiscectomy", PLOS One, Apr. 3, 2017, 11 pages.

Michael F. Coscia, MD et al, "*Propionibacterium acnes*, Coagulase-Negative *Staphylococcus*, and the "Biofilm-like" Intervertebral Disc", SPINE, vol. 41, No. 24, 2016, pp. 1860-1865.

Zhi Shan, MD et al, "*Propionibacterium acnes* Incubation in the Discs Can Result in Time-Dependent Modic Changes", SPINE, vol. 42, No. 21, 2017, pp. 1595-1603.

Zhi Shan, MD et al, "The influence of Direct Inoculation of *Propionibacterium acnes* on Modic Changes in the Spine", The Journal of Bone and Joint Surgery, 2017, pp. 477-481 (plus cover page).

EPO Art. 94(3) Communication in EP appl. No. 18879170.1, dated Oct. 17, 2022 (6 pp.).

\* cited by examiner

COMPOSITIONS AND METHODS FOR TREATING INTERVERTEBRAL DISCS

CROSS-REFERENCE TO RELATED APPLICATIONS

This is a national stage entry of international application PCT/US2018/061665 which claims the benefit of U.S. provisional patent application Nos. 62/588,401, filed 19 Nov. 2017, and 62/748,431, filed 20 Oct. 2018.

BACKGROUND INFORMATION

*Propionibacterium acnes* (*P. acnes*), recently re-designated as *Cutibacterium acnes*, is one of the most commonly encountered bacteria in the human population. It constitutes a portion of the dermal flora of most adults, living on or in fatty acids from sebaceous gland secretions; it is considered largely commensal, although rapid growth can cause skin disorders such as folliculitis and acne vulgaris. Although tolerant of air, the *P. acnes* bacterium is anaerobic.

*P. acnes* can exist in both planktonic and biofilm forms. In the latter, bacteria interact with surfaces and form colonies and continue to grow while being protected by exopolysaccharide (EPS) and/or extracellular-polysaccharide (ECPS) macromolecules which crosslink to form matrices or films that also keep the bacteria attached to the surface. *P. acnes* grows more quickly when in biofilm film than in planktonic form, and the biofilm form of *P. acnes* is believed to be that involved in the aforementioned skin disorders.

The aforementioned biofilm matrices protect bacteria against many forms of attack. The small diameter of flow channels in the matrix restricts the size of molecules that can transport to the underlying bacteria, and functional groups on the EPS/ECPS macromolecules react or interact with biocides, which then are unavailable for action against the underlying bacteria.

Additionally, the majority of bacteria in biofilm form are down-regulated (sessile) and not actively dividing, which makes them resistant to attack by a large group of antibiotics and antimicrobials, many of which attack the bacteria during the active parts of their lifecycle, e.g., cell division. A small portion, usually those at the bottom, are sessile, yet these too are impervious to antibiotics due to inaccessibility, and this small portion can regrow the entire biofilm after a course of treatment is completed.

Since the beginning of the 21st century, a small but steady stream of journal articles have posited a link between spine-related conditions and *P. acnes*. For example, inflammation around the nerve root in patients with sciatica has been hypothesized to be caused by a chronic infection from gram-positive bacteria such as *P. acnes*; see, e.g., A. Stirling et al., "Association between sciatica and *Propionibacterium acnes*," *Lancet*, vol. 357, no. 9273, pp. 2024-25 (2001) and A. Stirling et al., "Association Between Sciatica and Skin Commensals," *J. Bone & Joint Surgery*, 84:B (Supplement II):147 (2002). Others who have cultured lumbar discs after surgery likewise report having found gram-positive bacteria; see, e.g., M. N. Capoor et al., "Prevalence of *Propionibacterium acnes* in Intervertebral Discs of Patients Undergoing Lumbar Microdiscectomy: A Prospective Cross-Section Study," *PLoS One*, 11(8):e0161676 (2016).

The foregoing studies have been the subject of criticism due to, inter alia, small sample sizes, use of qualitative techniques (positive/negative without regard to prevalence), and the difficulty in ensuring that *P. acnes* present in cultured samples did not come from peri- or post-operative contamination. A study designed to address these types of issues claims to have found *P. acnes* in nearly one-third of samples; see M. N. Capoor et al., "*Propionibacterium acnes* biofilm is present in intervertebral discs of patients undergoing microdiscectomy," *PLoS One*, 12(4):e0174518 (2017). The paper also describes identification of *P. acnes* biofilms in the disc tissue.

Other types of bacteria have been described as being present in compromised intervertebral discs; see, for example, X. Chevalier et al., "Iatrogenically induced vertebral osteomyelitis due to *Pseudomonas aeruginosa,*" *Clin. Exp. Rheumatol.*, 14(2), pp. 191-94 (1996), and M. F. Coscia et al, "*Propionibacterium acnes*, Coagulase-Negative *Staphylococcus*, and the 'Biofilm-like' Intervertebral Disc, *SPINE*, vol. 41:34, pp. 1860-65 (2016).

Those suffering from vertebrae-related conditions, including but not limited to bulging discs and herniated discs, as well as other spine-related conditions such as sciatica, usually must choose between pain management and surgery, with few intermediate options available. Steroids, usually introduced via injection, sometimes are prescribed so as to reduce or mitigate against inflammation.

Compositions and non-surgical methods capable of treating such conditions, either to prevent worsening or to reverse existing symptoms, are of significant interest.

SUMMARY

Provided herein are antimicrobial compositions effective against microbial biofilms, including in vivo macrostructures (e.g., biofilms) of bacteria. The compositions are biocompatible, and most embodiments have little or no toxicity to vertebrates, including mammals and specifically humans, permitting the composition to be delivered to and used near the spinal column of such vertebrates.

Once introduced to an area colonized with a bacterial macrostructure, particularly an intervertebral disc, the antimicrobial composition weakens the EPS/ECPS macromolecules of the protective film. As the integrity of the protective biofilm is compromised or interrupted, the entire biofilm structure might be susceptible to being dislodged from the affected area or biosorbed. Additionally or alternatively, certain of the subcomponents of the solute component, as well as perhaps the organic liquid(s) of the solvent component, might lyse microbes, particularly gram-positive bacteria, previously protected by the EPS/ECPS macromolecules.

The form of the composition can vary to accommodate the time and method of introduction to an affected area, as well as the particular area to be treated.

One embodiment involves a flowable liquid antimicrobial composition that can be used to flush the area of an affected intervertebral disc during or immediately after a surgical procedure. While an intervertebral disc, or the surrounding area, is subjected to a surgical procedure, a flowable liquid composition can be introduced so as to act on microbial biofilms in that area. Advantageously, such a composition is sufficiently biocompatible so as to not require removal or flushing. Depending on the manner of delivery, such a composition also might assist in dislodging a biofilm.

Another embodiment involves a less flowable antimicrobial composition, one which tends to stay in place when applied to an affected intervertebral disc (or surrounding area) and then biosorbs slowly so as to provide an extended dwell time on or near the affected area. The effective solute concentration of this type of composition can be relatively moderate (on the order of 650 mOsm/L or less, often from 120 to 400 mOsm/L) or, where the composition is carried in a vehicle that permits elution or release of the composition over a more extended period of time, quite a bit higher (at least 750 mOsm/L, at least 875 mOsm/L, or at least 1 Osm/L, with 20-30% higher values being permitted where the gel carrier provides very slow release).

The different physical forms in which the composition can be provided permit it to be delivered and used in a variety of ways, and various methods of introducing and using the compositions also are provided herein.

Regardless of physical form, the antimicrobial composition includes a solvent component and a solute component.

The solute component of the antimicrobial composition includes a buffer precursor, i.e., a weak acid and the salt of weak acid, often a conjugate base of the weak acid. The solute component also optionally can include at least one additional weak acid, particularly a weak acid known to be not well tolerated by at least *P. acnes*. The weak acid(s) and salt(s) constitute the majority of solutes in the composition, with the acids also believed to be effective at interrupting or breaking ionic crosslinks in the macromolecular matrix of the biofilm, thereby facilitating passage of solutes and surfactant through the matrix to microbes entrained therein and/or protected thereby.

In some embodiments, the solute component of the antimicrobial composition also can include at least one surfactant, often added up to the maximum permitted per-dosage amount, regardless of the amount/physical form of composition employed. Enhanced efficacy often is seen when an ionic surfactant is employed.

The solvent component of the antimicrobial composition includes water and at least one organic liquid that has low cytotoxicity and is well tolerated by organs and tissues potentially contacted by the composition. The identity and amount of the organic liquid(s) preferably are chosen so that the solvent component exhibits a $\delta_p$ value of less than 15.2 MPa$^{1/2}$, preferably less than 14.9 MPa$^{1/2}$, and even more preferably less than 14.7 MPa$^{1/2}$, where $\delta_p$ is the dipolar intermolecular force (polarity) Hansen Solubility Parameter (HSP).

(HSP is a common method for predicting whether one material will dissolve in another to form a solution. U.S. Pat. No. 10,021,876 includes extensive descriptions of HSP, Hansen space ($R_a$), interaction radius ($R_0$), Relative Energy Difference (RED), calculation of $\delta_p$ for a multi-liquid solution, $\delta_p$ values for a variety of organic liquids, etc., and the interested reader is directed there for additional information.)

Hereinthroughout, the $\delta_p$ value for a given solvent or combination of solvents is determined at room temperature (solubility typically increases with increasing temperature, meaning that the dissolution rate of the macromolecular matrix and the bacterial cell wall proteins will increase, so the efficacy of the inventive composition is expected to increase at higher temperatures), and pH values are those which can be obtained from any of a variety of potentiometric techniques employing a properly calibrated electrode.

DETAILED DESCRIPTION OF ILLUSTRATIVE EMBODIMENTS

As summarily explained above, the present antimicrobial compositions include solvent and solute components, each of which is described separately.

The solvent component typically includes water ($\delta_p$~16.0 MPa$^{1/2}$) and at least one organic liquid with a $\delta_p$ value lower than that of water.

The $\delta_p$ value of the overall solvent component is less than 15.5, generally less than 15.3, less than 15.2, or less than 15.1, preferably no more than 15.0, no more than 14.9, no more than 14.8, no more than 14.7, or even no more than 14.6 MPa$^{1/2}$. In those embodiments involving a less flowable antimicrobial composition, one which tends to stay in place when applied to an affected intervertebral disc (or surrounding area) and then biosorb slowly, each of the foregoing values can be reduced by 10-20%.

The solvent component can consist of, or consist essentially of, water and one organic liquid having $\delta_p$ value less than 15.5 MPa$^{1/2}$. In other embodiments, the solvent component can consist of, or consist essentially of, water and two or more organic liquids with the resulting solvent component having $\delta_p$ value less than 15.5 MPa$^{1/2}$. In still other embodiments, water can be replaced in whole or in part with dimethyl sulfoxide (DMSO).

Water is desirable due to its high solute loading capacity (which allows for higher osmolarity compositions), wetting properties, excellent biocompatibility, environmental friendliness, and low cost. The intended usages of the present compositions argue for using purified water, particularly distilled, deionized, or similar.

The solvent component also contains one or more organic liquids, which act(s) to, inter alia, reduce the $\delta_p$ value of the solvent component to a point where it can better solubilizes one or more of the proteins of the cell walls of bacteria of interest, including gram-positive bacteria such as *P. acnes*. Using terminology from U.S. Pat. No. 10,021,876, the organic liquid(s) adjust the $R_a$ of the solvent component to less than or equal to the $R_0$ of at least one bacterial cell wall protein, i.e., the solvent system-protein RED is no more than ~1.0. Solvating some portion of the cell wall proteins can induce membrane leakage, leading to cell lysis, thereby killing even those bacteria in a sessile state. By bringing some portion of these cell wall proteins into solution, the entrained gram positive bacteria more easily can be caused to lyse which, combined with the high partial pressure across their cell walls, leads to death of the microbe.

The reduced $\delta_p$ value of the solvent component also can permit the composition to effectively break down or bypass and disable the macromolecular (EPS/ECPS) defenses of a biofilm. Again using terminology from U.S. Pat. No. 10,021,876, the organic liquid(s) adjust the $R_a$ of the solvent component to less than or equal to the $R_0$ of one or more organic components of the macromolecular network. Enhancing macromolecular matrix dissolution and increasing its solubility in the solvent system permits a shorter mean free path for subcomponents of the solute component, thereby increasing their rate and density and decreasing their necessary contact time and/or severity. This can enhance the activity of the overall composition by facilitating access to bacteria by subcomponents of the solute component.

The foregoing solvent component $\delta_p$ values can be achieved by adding any of a variety of organic liquids to water (or vice versa).

The dipole-dipole interaction Hansen solubility parameter for a particular solvent component can be calculated according to the following formula:

$$\delta_p = \sum_{i=1}^{n} (\delta_{di} \times x_{di}) \qquad (I)$$

where $\delta_{di}$ is the energy from dipolar intermolecular force for solvent subcomponent i, $x_{di}$ is the percentage of subcomponent i in the solvent component, and n is the total number of subcomponents. The amount of a given organic liquid (or mixture of organic liquids) to be added to water can be calculated using formula (I) if a targeted $\delta_p$ value is known. Similarly, a projected $\delta_p$ value can be calculated using formula (I) if the amount of organic liquid(s) and their individual $\delta_p$ values are known.

The dipolar intermolecular force values for many organic liquids are readily available from a variety of sources, with values for many alcohols and glycol ethers having been compiled in U.S. Pat. No. 10,021,876.

Practically any organic liquid(s) having a $\delta_p$ value less than 6, less than 7, less than 8, less than 9, less than 10, less than 11, less than 12, less than 13, less than 14, less than 14.2, less than 14.4, less than 14.6, less than 14.8, or less than ~15 MPa$^{1/2}$ can be used to provide a solvent component having one of the aforementioned overall $\delta_p$ values. Non-limiting examples of potentially useful organic liquids include, with $\delta_p$ values in parentheses, $C_2$-$C_8$ alcohols such as ethanol (8.8 MPa$^{1/2}$) and isopropyl alcohol (6.1 MPa$^{1/2}$), sugar alcohols such as sorbitol (14.1 MPa$^{1/2}$) and xylitol (15.2 MPa$^{1/2}$), glycerin (12.1 MPa$^{1/2}$), polyols such as ethylene glycol (11.0 MPa$^{1/2}$), propylene glycol (9.4 MPa$^{1/2}$), and diethylene glycol (12.0 MPa$^{1/2}$) and alkylene glycol monoalkyl ethers such as ethylene glycol monomethyl ether (9.2 MPa$^{1/2}$), diethylene glycol monoethyl ether (9.2 MPa$^{1/2}$), triethylene glycol monoethyl ether (6.8 MPa$^{1/2}$), dipropylene glycol monopropyl ether (2.9 MPa$^{1/2}$) and diethylene glycol monomethyl ether (7.8 MPa$^{1/2}$). Other potentially useful organic liquids include, but are not limited to, ketones such as acetone, methyl butyl ketone and methyl ethyl ketone; acetates such as amyl acetate and ethyl acetate; (meth)acrylates; aryl compounds such as toluene and phenol; and aliphatic alkanes such as heptane, although the intended end use calls for use of only those amounts of any given organic liquid considered to be safe for use in the body.

When selecting such organic liquids for use in the solvent component of the composition, possible considerations include avoiding those which contain a functional group that will react with either the acid(s) or salt(s) employed in the composition and favoring those which possess higher regulatory pre-approval limits.

When used in conjunction with water, such a material(s) commonly is present at concentrations of from 1 to ~25%, 2.5 to 22.5%, 3 to 21%, 4 to 20%, 5 to 19%, 6 to 18%, 7.5 to 17.5%, 8 to 16%, and 10 to 15%, with all of the foregoing representing w/v measurements, i.e., grams of organic liquid(s) per liter of total solvent component of the composition.

Although the presence of water in the solvent component is preferred for reasons explained above, an organic liquid or a mixture of multiple organic liquids, one or more of which have a $\delta_p$ value less than 15.5 MPa$^{1/2}$ or the solution thereof having an overall $\delta_p$ value less than 15.5 MPa$^{1/2}$, that can solvate the solute component (and other optional ingredients, if present) without the presence or addition of water are contemplated. Thus, in certain embodiments, the solvent component can consist of, or consist essentially of, just organic liquids.

In the foregoing type of solvent component which includes only organic liquids, one liquid of potential utility is DMSO. It has a $\delta_p$ value similar to that of water (16.4 MPa$^{1/2}$), but its organic nature permits it to carry and transport drugs into body tissues. Accordingly, DMSO preferably is used in place of, or in addition to, water where the solute component (discussed below) includes an antibiotic or other pharmaceutically active compound.

The antimicrobial composition also includes a solute component, which includes subcomponents designed to counteract different defenses of the target bacterium and its various biofilm defenses. The amount of the subcomponents of the solute component are sufficient to provide an overall effective solute concentration to the composition which permits inducement of cell lysis when the composition encounters a targeted bacterium.

A viable way to determine effective solute concentrations for a given composition is through calculations based on the following general formula:

$$\text{Osmolarity} = \sum_{i=1}^{n} \varphi_i x_i C_i \quad \text{(II)}$$

where $\varphi$ is the osmotic coefficient for solute subcomponent i, x is the number of species into which that solute subcomponent can dissociate (taking into account the pH of the solution, where necessary), and C is the molar concentration of that solute subcomponent. The coefficient is designed to account for non-ideality of the solution. While some compounds can have a coefficient that is greater than 1 (e.g., sucrose), ionic compounds tend to have coefficients which are less-than-one to reflect the impact of, e.g., electrostatic effects. Coefficients are tabulated at a variety of locations including, for example, R. A. Robinson et al., "Tables of Osmotic and Activity Coefficients of Electrolytes in Aqueous Solution at 25° C.," *Trans. Faraday Soc.*, 45, pp. 612-24 (1949; Royal Society of Chemistry; London, England) and W. J. Hamer et al, "Osmotic Coefficients and Mean Activity Coefficients of Uni-valent Electrolytes in Water at 25° C.," *J. Phys. Chem. Ref Data*, vol. 1, no. 4, pp. 1047-99 (1972; U.S. Secy. of Commerce; Washington, D.C.). For many of the solute subcomponents described below, a coefficient of near unity can be presumed.

Where a measured effective solute concentration is desired, one must keep in mind the difficulties presented by the present antimicrobial compositions. Standard osmometry techniques such as freezing point depression or boiling point elevation might yield anomalous results because the concentrations of solutes in these compositions typically are higher than those usually measured in microbiology laboratories (normal saline solutions are on the order of 300 mOsm/L), and their solvent components typically involve more than one type of liquid (i.e., the solvent component is not just water).

If a measured effective solute concentration is desired, options include thermal analysis (e.g., DSC or TGA) and measurement of a modified colligative property determination. Regarding the latter, the impacts of the presence of any organic liquid(s) and surfactant(s) (if any) must be taken into account which can be accomplished by performing the osmometry technique (e.g., freezing point depression) on a proxy solution in which surfactant(s) are omitted and any organic liquid(s) are replaced with an equal volume of water. The former is acceptable because surfactants have a negligible effect on effective solute concentration, given the very small amounts employed (as described below), and the latter also is acceptable because colligative properties are essentially independent of the nature of the solvent as long as the degree of solubilization of solutes is similar.

Because osmolarity is a colligative property, the contribution to efficacy attributable to high effective solute concentration is substantially independent of the particular identity or nature of individual subcomponents of the solute component. Nevertheless, as a general rule, smaller molecules tend to be more effective than larger molecules due to solvent capacity (i.e., the ability to (typically) include more small molecules in a given amount of solvent component than an equimolar amount of larger molecules), relative ease of transport through the macromolecular matrix of a biofilm, and ease of transport across cell wall membranes. Additionally, charged, chelating molecules increase dissolution of the macromolecular matrix by removing the crosslinking metal ions between EPS chains, and accordingly are a preferred class of solutes.

One approach to achieve increased osmolarity of the composition is by adding large amounts of ionic compounds (salts); see, e.g., U.S. Pat. No. 7,090,882.

Efficacy of a composition generally increases as its osmolarity (effective solute concentration) increases. The presence of an abundance of solute subcomponents helps to induce a high osmotic pressure across the bacterial cell wall membranes, leading to lysis.

The intended location of use of the present antimicrobial compositions argues for an effective solute concentration below that which might be able to be used on an inanimate object or surface. Nevertheless, efficacy can be maintained as long as a threshold effective solute concentration value necessary to induce an osmotic pressure imbalance across the bacterial cell wall is maintained.

In embodiments where the antimicrobial composition is provided in a non-viscous liquid form, the effective solute concentration of the composition generally is at least 100, 120 or 125 mOsm/L, typically 125 to 275 mOsm/L, 120 to 300 mOsm/L, or 100 to 325 mOsm/L. The upper limit for effective solute concentration is no more than about 1.10, typically no more than 1.05, and commonly no more than 1.0 Osm/L, although regulatory or other standards setting bodies might prescribe lower upper limits such as, for example, 900, 800, 750, 700, 650, 600, 575 or even 550 mOsm/L. Ranges of useful effective solute concentrations based on various combinations of the foregoing minimum and maximum values are contemplated, with preferred ranges including 125 to 675 mOsm/L, 130 to 625 mOsm/L, 135 to 600 mOsm/L, 140 to 575 mOsm/L, and 150 to 550 mOsm/L.

These foregoing osmolarity values might be amenable to being downwardly adjusted if the physical characteristics of the composition are such that it can stay in or on the affected area for extended periods of time. One manner for achieving extended contact times is by employing a viscosity enhancing additive, such as a gel carrier for the composition, e.g., polyethylene glycol (PEG) or polyvinylpyrrolidone (PVP). A composition provided as a semi-viscous gel permit solute components can elute over time, allowing for use of a composition with a somewhat greater effective solute concentration. Particular carrier vehicles can be chosen to provide control over elution rate from the gel to provide long-term application of the antimicrobial composition.

This form of the composition tends to stay in place when applied to an affected intervertebral disc (or surrounding area) and then biosorb slowly so as to provide an extended dwell time on or near the affected area. The effective solute concentration of this type of composition can be relatively moderate, on the order of 1.0 Osm/L or less, often less than 750 mOsm/L. Exemplary effective solute concentrations for a composition employed to make a semi-viscous gel include, but are not limited to, 100 to 500, 100 to 600, 100 to 700, 100 to 800, 100 to 900, 100 to 1000, 200 to 400, 200 to 500, 200 to 600, 200 to 700, 200 to 800, 200 to 900, 200 to 975, 250 to 350, 250 to 450, 250 to 550, 250 to 650, 250 to 750, 300 to 400, 300 to 450, 300 to 500, 300 to 600, 300 to 700, 300 to 750, 400 to 500, 400 to 600, 400 to 700, 400 to 800, 400 to 900, 400 to 1000, 450 to 500, 450 to 550, 450 to 600, 450 to 650, 450 to 700, 450 to 750, 500 to 550, 500 to 600, 500 to 650, 500 to 700, 500 to 750, 550 to 600, 550 to 650 and 550 to 700 (all of the foregoing being mOsm/L).

Gel carriers which provide very slow elution rates, permitting release of the composition over a very extended period of time. These alternative embodiments permit use of compositions having higher effective solute concentrations, on the order of 1.3 Osm/L or more, often 1.35 to 1.55 Osm/L. Exemplary effective solute concentrations for a composition employed to make a slow eluting gel include, but are not limited to, 0.5 to 2.0, 0.7 to 1.8, 1.0 to 1.5, 0.5 to 1.8, 0.5 to 1.0, 0.7 to 1.0, 0.7 to 1.3, 0.7 to 1.5, 0.8 to 1.8, 1.0 to 1.8, and 1.0 to 1.3 (all of the foregoing being Osm/L).

Advantageously, by employing a solvent component with an appropriately tailored $\delta_p$ value, the efficiency of the composition with respect to both macromolecular matrix dissolution and inducement of cell lysis can be maintained even when employing lower effective solute concentrations than in similar compositions described previously. In other words, lower osmolarity compositions can provide greater efficacy than counterpart compositions that employ only water in the solvent component. Nevertheless, keeping the effective solute concentration of the composition as high as possible while simultaneously tailoring the aforementioned solvent polarity parameter(s) assists delivering osmotically active solutes to microbes typically well protected by a biofilm's macromolecular matrix and cell wall proteins.

Antibacterial efficacy resulting from the relatively high effective solute concentration just discussed can be positively impacted by including sufficient acid to move the pH away from neutral. Acid is preferred over base in this end use application because of the body cavity's somewhat acidic pH (hence increased tolerance) and the sensitivity of the targeted types of bacteria to acids.

While near neutral pH compositions (e.g., $6.5 \leq pH \leq 7.5$) have efficacy in some applications, the pH of the composition for this application typically is moderately low, e.g., a pH of at least about 5.0, 5.2, 5.4, 5.5, 5.6, 5.8, 6.0 or 6.2 up to near neutral. The composition generally has a pH of from ~4.5 to ~7.1, from ~4.6 to ~7.0, from ~4.7 to ~6.9, from ~4.8 to ~6.8, from ~4.9 to ~6.7, or from ~5.0 to ~6.5.

In general, lower pH values correlate with enhanced efficacy due to an increase in the driving force for chelation of the metal ions crosslinking the EPS polymers, i.e., more efficient disruption (or at least swelling) of the macromolecular matrix of a biofilm. As the protection afforded by the macromolecular matrix is interrupted or decreased, passage of solutes through the matrix to microbes entrained therein and/or protected thereby is facilitated, thereby increasing the rate of cell lysis. This enhancement may not be linear, i.e., the enhancement in efficacy may be asymptotic past certain hydronium ion concentrations.

Acidity can be achieved by adding to the solvent component (or vice versa) one or more acids. Strong (mineral) acids such as HCl, $H_2SO_4$, $H_3PO_4$, $HNO_3$, $H_3BO_3$, and the like or, preferably, weak acids, particularly organic polyacids may be used. Examples of weak acids include monoprotic acids such as formic acid, acetic acid and substituted variants (e.g., hydroxyacetic acid, chloroacetic acid, dichloroacetic acid, phenylacetic acid, and the like), propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (e.g., oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different.

In certain embodiments, preference can be given to those weak acids which are, or can be made to be, highly soluble in aqueous systems; acids that include groups that enhance solubility in water (e.g., hydroxyl groups), examples of which include tartaric acid, citric acid, and citramalic acid, can be preferred in some circumstances. In these and/or other embodiments, preference can be given to those weak acids which are biocompatible. Alternatively or additionally, preference can be given to those weak acids which can act to chelate the metallic cations involved in crosslinking the macromolecular matrix of the biofilm.

The solute component optionally can include a mixture of weak acids, particularly at least one additional weak acid known to be not well tolerated by P. acnes, e.g., salicylic acid, as well as a polyacid such as citric acid.

The amount of acid to be added can be calculated or can be added until the composition reaches a desired pH, using standard pH monitoring equipment to track increases.

Employing large amounts of weak acids in the solute component can negatively impact biocompatibility by driving down the pH of the composition below an acceptable value. To avoid going past a physiologically acceptable pH while still raising the effective solute above a targeted threshold, the solute component of the antimicrobial composition can include a buffer precursor, i.e., a weak acid and a salt of that or another weak acid. The weak acid(s) and salt(s) constitute the majority of solutes in the solute component.

For example, a large amount of one or more salts of one or more weak acids can be included in the solute component. The molar amount of salt(s) employed can range from a significant fraction of the amount of acid(s) employed, e.g., 1:2, 2:3, 3:4, etc., to an excess relative to the acid(s), e.g., 4:3, 3:2 or 2:1 up to 10:1, typically up to 5:1, 4:1 or 3:1.

The identity of the countercation portion of the salt is not believed to be particularly critical, with common examples including ammonium ions and alkali metals. Where a polyacid is used, all or fewer than all of the H atoms of the carboxyl groups can be replaced with cationic atoms or groups, which can be the same or different. For example, mono-, di- and trisodium citrate all constitute potentially useful buffer precursors. However, because trisodium citrate has three available basic sites, it has a theoretical buffering capacity up to 50% greater than that of disodium citrate (which has two such sites) and up to 200% greater than that of sodium citrate (which has only one such site).

In some embodiments, the solute component of the antimicrobial composition also can include at least one surfactant, often added up to the maximum permitted per-dosage amount, regardless of the amount/physical form of composition employed. Enhanced efficacy often can be achieved by inclusion of ionic surfactant(s).

Low concentrations of surfactant can be used. The presence of a surfactant, particularly a polar surfactant, increases the efficacy of these formulations and increases the rate at which the composition acts against the targeted microbe(s). This is most likely due to the surfactant inducing cell lysis by attaching to those portions of the cell wall proteins that are solubilized by the solvent component.

In the compositions described in U.S. Patent Publ. Nos. 2010/0086576 and 2014/0242188, inclusion of a surfactant, preferably an ionic surfactant, is required. In the composition described in U.S. Pat. No. 10,021,876, surfactant is not required, although inclusion of a surfactant is said to increase the ability to both solubilize EPS polymers (by binding to those polymers and bringing them into solution) and by helping to extract proteins from bacterial cell walls, leading to cell leakage and lysis. The present compositions follows the teaching of the latter, i.e., the presence of one or more inorganic liquids in the solvent component at times can permit omission, or at least reduction(s) in the amount(s), of surfactant(s).

Essentially any material having surface active properties in water can be employed, regardless of whether water is present in the solvent component of the composition, although those that bear some type of ionic charge are expected to have enhanced antimicrobial efficacy because such charges, when brought into contact with a bacteria, are believed to lead to more effective cell membrane disruption and, ultimately, to cell leakage and lysis. This mechanism can kill even sessile bacteria because it does not involve or entail disruption of a cellular process.

Polar surfactants generally are more efficacious than non-polar surfactants. Ionic surfactants are most effective because they can directly interact with EPS polymers and bacterial cell wall proteins. For polar surfactants, cationic surfactants are the most effective, followed by zwitterionic and anionic surfactants. Additionally, smaller surfactants are more efficacious because they can more easily move through the biofilm macromolecular matrix and access the entrained bacteria. Another factor which influences the efficacy of ionic surfactants is the size of side-groups attached to the polar head. Larger size-groups and more side-groups on the polar head can decrease the efficacy of surfactants.

Because surfactant is not the only component in the present composition involved in solubilizing proteins (i.e., solvent assists in this process), non-ionic surfactants can be more effective than they were found to be in prior compositions not containing solvent.

Potentially useful nonionic surfactants include, but are not limited to, sodium polyoxyethylene glycol dodecyl ether, N-decanoyl-N-methylglucamine, digitonin, n-dodecyl ß-D-maltoside, octyl β-D-glucopyranoside, octylphenol ethoxylate, polyoxyethylene (8) isooctyl phenyl ether, polyoxyethylene sorbitan monolaurate, and polyoxyethylene (20) sorbitan cholamidopropyl) dimethylammonio]-2-hydroxy-1-propane sulfonate, 3-[(3-cholamidopropyl) dimethylammonio]-1-propane sulfonate, 3-(decyldimethylammonio) propanesulfonate inner salt, and N-dodecyl-N,N-dimethyl-3-ammonio-1-propanesulfonate.

Potentially useful zwitterionic surfactants include sulfonates (e.g. 3-[(3-cholamidopropyl)dimethylammonio]-1-propanesulfonate), sultaines (e.g. cocamidopropyl hydroxysultaine), betaines (e.g. cocamidopropyl betaine), and phosphates (e.g. lecithin).

Potentially useful anionic surfactants include, but are not limited to, ammonium lauryl sulfate, dioctyl sodium sulfosuccinate, perflourobutanesulfonic acid, perfloruononanoic acid, perfluorooctanesulfonic acid, perfluorooctanoic acid, potassium laurylsulfate, sodium dodeylbenzenesulfonate, sodium laureth sulfate (SLS), sodium lauroyl sarcosinate, sodium myreth sulfate, sodium pareth sulfate, sodium stearate, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (SDS), sodium glycodeoxycholate, sodium lauryl sulfate, and the alkyl phosphates set forth in U.S. Pat. No. 6,610,314.

Potentially useful cationic surfactants include, but are not limited to, cetylpyridinium chloride (CPC), cetyl trimethylammonium chloride, benzethonium chloride, 5-bromo-5-nitro-1,3-dioxane, dimethyldioctadecylammonium chloride, cetrimonium bromide, dioctadecyl-dimethylammonium bromide, tetradecyltrimethyl ammonium bromide, any of a variety of benzalkonium chloride (BK) compounds, hexadecylpyridinium chloride monohydrate and hexadecyltrimethylammonium bromide, with the benzalkonium chloride being a preferred material.

For other potentially useful materials, the interested reader is directed to any of a variety of other sources including, for example, U.S. Pat. Nos. 4,107,328, 6,953,772, and 7,959,943.

Preferred surfactants in the present composition are CPC, SLS, or a benzalkonium halide such as stearalkonium chloride.

When a surfactant is included in the solute component, the amount can vary widely based on a variety of factors including, but not limited to, the age of the biofilm (particularly whether it is entrenched, a factor which relates to the type of proteins and mass of the macromolecular matrix), size of the biofilm, whether the targeted species of bacterium is present with other type(s) of bacteria, and the solubility of the surfactant(s).

The amount of surfactant generally constitutes greater than ~0.01%, typically at least ~0.02%, typically at least ~0.03%, typically at least ~0.04%, and typically at least ~0.05% (all w/w, based on the total weight of the composition). Some compositions can include even more surfactant, for example, at least ~0.12%, at least ~0.13%, at least ~0.14%, at least ~0.15%, at least ~0.16%, at least ~0.2%, at least ~0.25%, at least ~0.33%, at least ~0.35%, and even at least 0.5% of the composition (all w/w, based on the total weight of the composition). (Any two of the foregoing minimum amounts can be combined to provide an exemplary range of amounts of surfactant.) The practical upper limit of amount of surfactant to be incorporated can be defined by the solubility limits of the particular surfactant(s) chosen, although typically the upper limit will be capped by regulatory or standards setting bodies, with nonionic surfactants likely having higher maximum amounts (e.g., 0.25-0.35 g/L) than those materials which include some type of ionic character (e.g., 0.01-0.02 g/L).

Given the intended end uses for the composition, inclusion of inactive materials, i.e., adjuvants, typically is not preferred, but there presence can be permitted in certain circumstances. Examples of such adjuvants include, but are not limited to, emollients, fungicides, pigments, dyes, defoamers, foaming agents, abrasives, bleaching agents, preservatives (e.g., antioxidants) and the like. A comprehensive listing of additives approved by the U.S. Food and Drug Administration is available (by hyperlink to a zipped text file) at http://www.fda.gov/-Drugs/InformationOnDrugs/ucm113978.htm (link active as of filing date of this application).

The composition does not require inclusion of an active antimicrobial agent for efficacy, but such materials can be included in certain embodiments. Non-limiting examples of potentially useful active antimicrobial additives include aldehydes such as gluteraldehyde, formaldehyde, and o-phthalaldehyde; formaldehyde-generating compounds such as noxythiolin, tauroline, hexamine, urea formaldehydes, imidezolone derivatives, and the like; anilides, particularly triclocarban; biguanides such as chlorhexidine and alexidine, as well as polymeric forms such as poly(hexamethylene biguanide); dicarboximidamides (e.g., substituted or unsubstituted propamidine) and their isethionate salts; halogen atom-containing or releasing compounds such as a bleach solution, $ClO_2$, dichloroisocyanurate salts, tosylchloramide, iodine (and iodophors), and the like; silver and silver compounds such as silver acetate, silver sulfadiazine, and silver nitrate; peroxides such as $H_2O_2$ and peracetic acid; phenols, bis-phenols and halophenols (including hexachlorophene and phenoxyphenols such as triclosan); and quaternary ammonium compounds. Additionally, antibiotics may be added for medical applications.

Particularly in situations where DMSO replaces some or all of the water in the solvent component, the solute component of the composition can include at least pharmaceutically active compound.

Based on the foregoing description, one can see that the non-solvent portion of the composition can consist of, or consist essentially of, species resulting from dissociation of buffer precursor components (e.g., weak acid and a salt) and, optionally, one or more surfactants.

The composition conveniently can be provided as a solution, as a ready-to-use product or as a concentrate, although other forms might be desirable for certain end-use applications. Accordingly, the composition can provided as a soluble powder (for subsequent dilution, an option which can reduce transportation costs), or a thicker form such as a gel or paste which might be particularly useful for providing increased residence times.

The composition can also be provided as a gel or coating that actively elutes out to disinfect or prevent colonization of a surface. In a gel, a liquid form of the composition can be formulated into an oil/water emulsion or water-miscible carrier base. Oil/water bases can include hydrophilic ointment as well as those used in such commercial products as Dermabase™ Velvachol™, and Unibase™ ointments. Water-miscible bases include PEG ointment, cellulosic gels, chitosan gels, polyvinyl pyrollidone, and those used in such commercial products as Polybase™ ointment.

Examples of solvent-containing compositions that can be provided as stable gels are shown in Table 1. (By "stable" is meant no substantial loss in efficacy or change in appearance after room temperature storage for several months.) Each had an effective pH of 4.0; the first two had 10% w/v entrained solvent (DGME and IPA, respectively), while the third had 1% w/v entrained phenoxyethanol (because U.S. Food and Drug Administration regulations permit far less of this material in compositions intended for dermal contact).

TABLE 1

| Gel-form compositions (% by wt.) | | | |
| --- | --- | --- | --- |
|  | #1 | #2 | #3 |
| PEG 400 | 45 | 45 | 45 |
| PEG 3350 | 30 | 30 | 30 |
| BK | 0.14 | 0.14 | 0.14 |

TABLE 1-continued

| Gel-form compositions (% by wt.) | | | |
| --- | --- | --- | --- |
| | #1 | #2 | #3 |
| sodium citrate dihydrate | 3.57 | 3.57 | 3.57 |
| citric acid | 3.41 | 3.41 | 3.41 |
| solvent | 2.5 | 2.5 | 0.25 |
| water | 15.39 | 15.39 | 17.64 |

The aforedescribed compositions can be introduced or applied to affected areas in a variety of ways. Potentially useful methods of introduction include injection via syringe, direct irrigation and surgical placement.

Where an antimicrobial composition is employed as part of an invasive (surgical) procedure, an initial irrigation of the impacted area to rinse away or degrade a biofilm can be sufficient to permit natural healing or regenerative processes to reduce inflammation once the irritant is gone. Direct irrigation can involve a liquid (which remains a liquid after injection) or a liquid that gels or becomes significantly more viscous when exposed to body temperature and/or moisture content.

Alternatively, that initial irrigation can be accompanied by application of a longer eluting semi-solid form of the composition so as to continue to eradicate remaining bacteria, whether in planktonic or biofilm form. For example, a viscous gel or a solid that entrains or otherwise carries an eluting composition can be placed on or near an intervertebral disc or other tissue adjacent thereto.

An antimicrobial composition also can be used in a non-surgical procedure, specifically via injection. This means for introduction can involve a liquid (which remains a liquid after injection), a liquid that gels or becomes significantly more viscous when exposed to body temperature and/or moisture content, a liquid that solidifies when exposed to body temperature and/or moisture content, a gel, or a gel that solidifies when exposed to body temperature and/or moisture content. In this type of procedure, a needle of appropriate gauge (e.g., 22 gauge) can be used to introduce a liquid or gel, typically one having a dynamic viscosity of 125 mPa·s or less, typically from about 0.5 to about 120 mPa·s, and commonly from about 1 to about 100 mPa·s, so as to ensure smooth injection. More viscous liquids and gels (e.g., though having dynamic viscosities of from 125 to ~275 mPa·s) can be used in connection with larger gauge needles.

An intervertebral disc includes an outer fibrous toroidal structure made of variously oriented lamellae (annulus fibrosus) which surrounds a gel-like center (nucleus pulposus). Both the annulus fibrosus and nucleus pulposus are composed of differing amounts of water, collagen, and proteoglycans (PGs), with the amounts of water and PGs being greater in the latter because they form a gel-like substance that resists compression. Because the two structures of the disc are compositionally similar, either has the potential of being impacted by bacteria in planktonic or biofilm form, accordingly, either portions of the disc can be the target of one of the foregoing application/introduction procedures.

Once introduced to an intervertebral disc, or surrounding area, colonized with bacteria, particularly gram-positive bacteria such as *P. acnes*, the antimicrobial composition can lyse such bacteria. Even where the bacteria are present in biofilm form, the composition can weaken the EPS/ECPS macromolecules of the protective film and, as the integrity of the protective biofilm is compromised or interrupted, the entire biofilm structure might be susceptible to being dislodged from the affected area or biosorbed. Additionally or alternatively, certain of the subcomponents of the solute component, as well as perhaps the organic liquid(s) of the solvent component, might lyse the bacteria previously protected by the EPS/ECPS macromolecules.

Tissue, such as an intervertebral disc, that has a biofilm residing therein or thereon tends to be inflamed. Inflamed tissue often results in a pain signal, which could help to explain why patients who have undergone discectomy surgery still report pain, i.e., the surrounding area remains inflamed.

Advantageously, application of the composition to an infected area, particularly one where a biofilm, particularly one containing *P. acnes* bacteria, has been located, can result in reduced inflammation within a relatively short amount of time, for example, a few hours to a week or so, typically 1-5 or 2-4 days, with continued reduction being possible as the composition remains on or near the affected area, thereby removing or eliminating additional bacteria.

To assist in understanding the foregoing description, the following definitions that are intended to apply throughout (unless the surrounding text explicitly indicates a contrary intention):

"comprising" means including but not limited to the listed ingredients;

"consisting of" means including only the listed ingredients and minor amounts of impurities or materials typically found in or with those ingredients;

"consisting essentially of" means including only the listed ingredients, minor amounts of other ingredients that supplement the antimicrobial activity (less than 0.25% (w/v)) and/or provide a secondary effect that is desirable in view of the intended end use (less than 2.5% (w/v)), and/or inactive additives or adjuvants (less than 5% (w/v));

"microbe" means any type of microorganism including, but not limited to, bacteria, viruses, fungi, viroids, prions, and the like;

"antimicrobial" means inhibiting growth or viability of a pathogenic microorganism;

"active antimicrobial agent" means an antimicrobial agent that is effective only or primarily during the active parts of the lifecycle, e.g., cell division, of a microbe;

"biofilm" means a community of microbes, particularly bacteria, attached to a surface with the community members being contained in and/or protected by a self-generated macromolecular matrix;

"effective solute concentration" is the total moles of solute(s) present in dissolved form a liquid composition;

"entrenched biofilm" is a biofilm that has reached a steady state mass after a growth period of two or more days;

"buffer" means a compound or mixture of compounds having an ability to maintain the pH of a solution to which it is added within relatively narrow limits;

"buffer precursor" means a compound that, when added to a mixture containing an acid or a base, results in a buffer;

"weak acid" means an acid which only partially ionizes in water and is inclusive of all compounds which include a carboxyl group;

"polyacid" means a compound having at least two carboxyl groups and specifically includes dicarboxylic acids, tricarboxylic acids, etc.;

"organic liquid" means any chemical compound which is liquid at standard temperature and pressure and which contains at least one C—H bond;

"benzalkonium chloride" refers to any compound defined by the following general formula

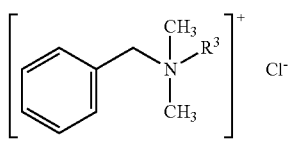

where $R^3$ is a $C_8$-$C_{18}$ alkyl group, or any mixture of such compounds;

"dwell time" means the amount of time that a composition contacts a biofilm;

"biocompatible" means presenting no significant, long-term deleterious effects on or in a mammalian species;

"biosorb" means to absorb a material into the body of a mammalian species;

"bleach solution" is an aqueous composition that contains from 4.0% to 6.5% (w/w) hypochlorite ion and has a 10≤pH≤12;

"soil load" means a solution of one or more organic and/or inorganic substances added to the suspension of a test organism to simulate the presence of body secretions, excretions, and the like;

"inoculum" means a solution containing bacteria, growth solution (e.g., tryptic soy broth) and protein soil load; and "substituted" means one containing a heteroatom or functionality (e.g., hydrocarbyl group) that does not interfere with the intended purpose of the group in question.

The relevant portions of any specifically referenced patent and/or published patent application are incorporated herein by reference.

The following examples are intended to provide specific details regarding specific embodiments of the aforedescribed composition, its production, and its use. Like embodiments set forth in the foregoing description, these are presented by way of example and not limitation. The appended claims and their equivalents define the breadth and scope of the inventive methods and compositions, and the same are not to be limited by or to any exemplary embodiment.

EXAMPLES

*Propionibacterium acnes* strain ATCC #6919 was grown in 50% strength reinforced clostridial medium (Becton Dickinson) under anaerobic conditions at 37° C. for 48 hours. A 500 μL aliquot of this broth was added to a 1 mL cryogenic vial, followed by 500 μL of a glycerol stock solution (20% w/v); each cryogenic vial was stored at −70° C. Overnight cultures were propagated from frozen stock by adding 100 uL of a frozen stock sample to 9.9 mL of 50% strength reinforced clostridial medium. This diluted sample was incubated overnight in an anaerobic chamber (37° C.) for use the following day.

Nucleus pulposis and annulus fibrosis tissue was harvested from fresh caudal discs obtained from split bovine spines harvested soon after slaughter by a local butcher. (More of the latter than the former was available, so three runs of the latter versus just one of the former were conducted.)

Using sterile scalpels, tissue explants were cut into small sections (1 cm diameters) which were sterilized with 4% paraformaldehyde (PFA) in phosphate-buffered saline (PBS), 10 minutes per mm of thickness, before being rinsed with and stored in sterile normal saline solution at 4° C. until needed for use.

At least two days prior to inoculation, the spinal tissue sections were rinsed with normal saline solution and then placed in conical vial containing double strength Dey Engley neutralizing broth (2×DE) and held at room temperature until inoculation.

On the day of inoculation, the tissue sections were rinsed with sterile normal saline solution before being placed in the wells of a 12-well microtiter plate. The plate was weighed after each tissue section was added, with the mass of each tissue section being recorded.

Each well was inoculated with 3 mL of a diluted form of the overnight culture (10% w/v in the 50% strength reinforced clostridial medium). After inoculation, the plate was covered and placed on a rocker in a 37° C. incubator set to 5% $CO_2$ so as to grow *P. acnes* biofilms on the tissue samples.

After 24 hours, the tissue sections were removed from the wells, placed in a second 12-well plate containing fresh normal saline solution to rinse away loosely attached bacteria (so as to ensure that the primary form of bacteria present would be in biofilm form). Each rinsed sample then was placed in a third 12-well plate, each well of which contained 3.0 mL of treatment or 3.0 mL normal saline solution as the control. This third treatment plate was covered and incubated in the same manner as described in the preceding paragraph.

After 24 hours, treated tissue sections were removed from the wells, and each was placed in a separate 10 mL portion of 2×DE. Each sample was vortexed (30 seconds), sonicated (120 seconds), and vortexed (30 seconds) to create a bacterial suspension which was serially 10-fold diluted and drop plated on 100% reinforced clostridial agar (Oxoid Ltd). In addition, 1.0 mL of the original cell suspension in 2×DE was plated.

The agar plates were incubated anaerobically at 37° C. for at least 96 hours before colonies on the plates were counted and the number of colony forming units (CFU) per gram (CFU/g) of tissue determined.

Table 2 below sets out the amounts of ingredients used to prepare five test solutions. Examples 1-3 are acidic, while Examples 4-5 are basic. Osmolality values were determined by taking the average of multiple freezing point depression tests of counterpart solutions where the organic liquid (i.e., ethanol or propylene glycol) was replaced with an equivalent amount of water.

TABLE 2 tested compositions

| Ingredient (each in g/L) | Ex. 1 | Ex. 2 | Ex. 3 | Ex. 4 | Ex. 5 |
| --- | --- | --- | --- | --- | --- |
| cetylpyridinium chloride | 1.2 | — | 1.2 | 1.2 | 1.2 |
| benzalkonium chloride | — | 0.2 | — | — | — |
| NaOH | — | — | — | 2.0 | 2.0 |
| $KH_2PO_4$ | — | — | — | 6.8 | 6.8 |
| citric acid | 7.7 | 7.7 | 7.7 | — | — |
| trisodium citrate dihydrate | 15.0 | 15.0 | 15.0 | — | — |
| ethanol | 200 | 200 | — | 200 | — |
| propylene glycol | — | — | 200 | — | 200 |

TABLE 2-continued tested compositions

| Ingredient (each in g/L) | Ex. 1 | Ex. 2 | Ex. 3 | Ex. 4 | Ex. 5 |
|---|---|---|---|---|---|
| Approximate $\delta_p$ of solvent component (MPa$^{1/2}$) | 14.6 | 14.6 | 14.7 | 14.6 | 14.7 |
| Measured osmolality (mol/kg) | 211 | 211 | 211 | 136 | 136 |
| Measured density (kg/L) | 1.010 | 1.010 | 1.010 | 1.004 | 1.004 |
| Osmolarity (mol/L) | 213 | 213 | 213 | 137 | 137 |

After each composition was prepared but before osmolality and density measurements were made, Examples 1-3 were titrated with a small amount of concentrated (37%, w/v) HCl so as to provide pH=5 solutions, while Examples 4-5 were titrated with a small amount of 50% (w/v) NaOH so as to provide pH=9 solutions.

Each of these compositions showed good efficacy in suspension time-kill screening tests (see ASTM E2315, 300 seconds) against *S. aureus* and *S. epidermidis* bacteria and were selected for testing against the aforedescribed intervertebral discs inoculated with *P. acnes*.

In the first round of static testing (i.e., the intervertebral disc was immersed in the composition), the compositions which included ethanol as the organic liquid (Examples 1-2 and 4) were 30 to 1000 times more effective than the compositions which included propylene glycol as the organic liquid (Examples 3 and 5). Accordingly, the ethanol-containing compositions were selected for repeat testing. The results of these tests are shown below in Table 3.

TABLE 3 efficacy against disc biofilms (log reductions)

| | Ex. 1 | Ex. 2 | Ex. 4 |
|---|---|---|---|
| first | 4.48 | 4.03 | 4.24 |
| second | 5.37 | 6.05 | 5.43 |
| third | 5.84 | 5.74 | 5.15 |
| average | 5.2 | 5.3 | 4.9 |

The numbers tabulated above are surprising, given that the tested compositions had such low effective solute concentrations and moderate pH values.

That which is claimed is:

1. A method for treating a spinal column area colonized with a biofilm that comprises at least one type of gram-positive bacterium which includes *P. acnes*, said area being an intervertebral disc or tissue adjacent thereto, said method comprising introducing via non-surgical injection to said area a liquid composition effective to weaken the macromolecules of said biofilm and, optionally, lyse the cell walls of one or more types of bacteria contained therein, said liquid composition having an effective solute concentration of 125 to 275 mOsm/L, said liquid composition consisting of a solvent component and a solute component, wherein said solvent component exhibits a $\delta_p$ value of less than 15.2 MPa$^{1/2}$ and consists of water and at least one organic liquid selected from the group consisting of ethanol and propylene glycol, and wherein said solute component consists of (i) citric acid, (ii) trisodium citrate dihydrate, and (iii) at least one cationic surfactant.

2. The method of claim 1 wherein said liquid has a dynamic viscosity of no more than about 125 mPa·s.

3. The method of claim 2 wherein said liquid increases in viscosity after said introduction.

4. The method of claim 3 wherein said liquid solidifies after said introduction.

5. The method of claim 1 wherein said liquid increases in viscosity after said introduction.

6. The method of claim 5 wherein said liquid solidifies after said introduction.

7. The method of claim 1 wherein said liquid composition has a pH of from 5.0 to 6.5.

8. The method of claim 1 wherein said solute component comprises less than 1% (w/v) of said cationic surfactant.

9. The method of claim 1 wherein said organic liquid is ethanol.

10. The method of claim 1 wherein said organic liquid is propylene glycol.

11. The method of claim 1, wherein said cationic surfactant is cetylpyridinium chloride.

12. The method of claim 1, wherein said cationic surfactant is benzalkonium chloride.

* * * * *